United States Patent
Donaldson (10) Patent No.: US 10,517,606 B1
(45) Date of Patent: Dec. 31, 2019

(54) INFLATABLE ARM SLEEVE

(71) Applicant: Robert Donaldson, Statesville, NC (US)

(72) Inventor: Robert Donaldson, Statesville, NC (US)

( * ) Notice: Subject to any disclaimer, the term of this patent is extended or adjusted under 35 U.S.C. 154(b) by 261 days.

(21) Appl. No.: 15/723,276

(22) Filed: Oct. 3, 2017

(51) Int. Cl.
| | |
|---|---|
| *A61B 17/135* | (2006.01) |
| *A61M 5/42* | (2006.01) |
| *A61L 31/14* | (2006.01) |
| *A61L 31/10* | (2006.01) |
| *A61B 17/00* | (2006.01) |

(52) U.S. Cl.
CPC ............ *A61B 17/135* (2013.01); *A61L 31/10* (2013.01); *A61L 31/146* (2013.01); *A61M 5/427* (2013.01); *A61B 2017/00477* (2013.01); *A61B 2017/00862* (2013.01)

(58) Field of Classification Search
CPC .............. A61B 17/135; A61B 17/1325; A61B 17/1355; A61B 2017/12004; A61B 17/132; A61B 5/02233; A61B 17/1322; A61B 2017/00557; A61F 5/012; A61H 9/0092
See application file for complete search history.

(56) References Cited

U.S. PATENT DOCUMENTS

| | | | |
|---|---|---|---|
| 5,190,530 A | 3/1993 | Greeff | |
| 5,413,582 A | 5/1995 | Eaton | |
| 7,468,048 B2 | 12/2008 | Meehan | |
| D668,396 S | 10/2012 | Shamis | |
| 8,834,517 B2 | 9/2014 | Croushorn | |
| 2007/0135835 A1* | 6/2007 | McEwen | A61B 17/1322 606/203 |
| 2008/0086070 A1* | 4/2008 | Meehan | A61F 5/0104 602/26 |
| 2016/0058653 A1 | 3/2016 | Oberdier | |

\* cited by examiner

*Primary Examiner* — Katherine M Shi (57) ABSTRACT

The inflatable arm sleeve prepares an arm to receive a hypodermic needle. The inflatable arm sleeve comprises a tubular bladder and a pump mechanism. The tubular bladder is further formed with a needle aperture. The tubular bladder is placed around the arm in the manner of a sleeve such that the needle aperture is positioned over the vein of the arm. The pump mechanism introduces compressed air into the tubular bladder such that pressure is applied to the arm from all directions around the arm except the needle aperture. The applied pressure will force blood into the unpressurized region of the vein underneath the needle aperture. The increase in pressure increases the diameter of the vein to make it easier to insert the hypodermic needle into the vein.

12 Claims, 7 Drawing Sheets

INFLATABLE ARM SLEEVE

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of medical and veterinary science including introducing media into the body, more specifically, a pumping device configured for use in introducing or removing media from the circulatory system.

SUMMARY OF INVENTION

The inflatable arm sleeve is configured for use with a patient. The patient is further defined with an arm. The arm is further defined with a vein. The inflatable arm sleeve is configured for use with a hypodermic needle. The inflatable arm sleeve prepares the arm to receive the hypodermic needle. The inflatable arm sleeve comprises a tubular bladder and a pump mechanism. The tubular bladder is further formed with a needle aperture. The tubular bladder is placed around the arm in the manner of a sleeve such that the needle aperture is positioned over the vein of the arm. The pump mechanism introduces compressed air into the tubular bladder such that pressure is applied to the arm from all directions around the arm except for the needle aperture. The applied pressure will force blood into the unpressurized region of the vein underneath the needle aperture. The increase in pressure increases the diameter of the vein to make it easier to insert the hypodermic needle into the vein. The inflatable arm sleeve further comprises a coating and a connector. The coating is an elastomeric material that: 1) forms a cushion that protects the arm from injury; and, 2) evenly distributes the pressure from the tubular bladder over the surface area of the arm.

These together with additional objects, features and advantages of the inflatable arm sleeve will be readily apparent to those of ordinary skill in the art upon reading the following detailed description of the presently preferred, but nonetheless illustrative, embodiments when taken in conjunction with the accompanying drawings.

In this respect, before explaining the current embodiments of the inflatable arm sleeve in detail, it is to be understood that the inflatable arm sleeve is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the inflatable arm sleeve.

It is therefore important that the claims be regarded as including such equivalent construction insofar as they do not depart from the spirit and scope of the inflatable arm sleeve. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Detailed reference will now be made to one or more potential embodiments of the disclosure, which are illustrated in FIGS. 1 through 9.

The inflatable arm sleeve 100 (hereinafter invention) is configured for use with a patient 191. The patient 191 is further defined with an arm 192. The arm 192 is further defined with a vein 193. The patient 191 refers to a person receiving treatment using the invention 100. The arm 192 refers to an arm 192 of the patient 191. The vein 193 refers to a vein 193 within the arm 192.

The invention 100 is configured for use with a hypodermic needle 194. The hypodermic needle 194 refers to a medical device that transfers media into and out of the body of the patient 191. The invention 100 prepares the arm 192 to receive the hypodermic needle 194. The invention 100 comprises a tubular bladder 101 and a pump mechanism 104. The tubular bladder 101 is further formed with a needle aperture 113. The tubular bladder 101 is placed around the arm 192 in the manner of a sleeve such that the needle aperture 113 is positioned over the vein 193 of the arm 192.

The pump mechanism 104 introduces compressed air into the tubular bladder 101 such that pressure is applied to the arm 192 from all directions around the arm 192 except for the needle aperture 113. The applied pressure will force blood into the unpressurized region of the vein 193 underneath the needle aperture 113. The increase in pressure increases the diameter of the vein 193 to make it easier to insert the hypodermic needle 194 into the vein 193.

The invention 100 further comprises a coating 102 and a connector 103. The coating 102 is an elastomeric material that: 1) forms a cushion that protects the arm 192 from injury; 2) evenly distributes the pressure from the tubular bladder 101 over the surface area of the arm 192, and 3) creates an insulated layer around the arm 192 that allows the body heat to warm the arm 192 which also makes the hypodermic needle 194 easier to insert into the vein 193. The connector 103 physically attaches the pump mechanism 104 to the tubular bladder 101.

The tubular bladder 101 is an inflatable structure. The tubular bladder 101 is a tubular structure. The tubular bladder 101 forms a sleeve. The arm 192 of the patient 191 inserts into the sleeve formed by the tubular bladder 101. As the tubular bladder 101 inflates, the tubular bladder 101 applies pressure to the arm 192. As described elsewhere in this disclosure, the tubular bladder 101 generates a differential pressure on the arm 192 which makes it easier to insert a hypodermic needle 194 into a vein 193 of the patient 191. The tubular bladder 101 comprises a shell 111, a chamber 112, and a needle aperture 113.

The shell 111 is a hollow tubular structure. The shell 111 has a hollow cylindrical shape. The shell 111 is formed from a gas impermeable material. The shell 111 forms a sealed hollow interior referred to as the chamber 112. The chamber 112 receives pressurized gas from the pump mechanism 104. The volume of the chamber 112 increases as the chamber 112 receives the pressurized gas from the pump mechanism 104. The increase in the volume of the chamber 112 decreases the inner diameter of the hollow cylindrical interior of the shell 111 such that pressure is applied to the arm 192 as the chamber 112 inflates.

The shell 111 comprises a first sheet 141 and a second sheet 142. The first sheet 141 is further defined with a first edge 161, a second edge 162, a third edge 163, and a fourth edge 164. The second sheet 142 is further defined with a fifth edge 165, a sixth edge 166, a seventh edge 167, and an eighth edge 168.

The first sheet 141 is a rectangular sheeting. The first sheet 141 is formed from a gas impermeable material. The first sheet 141 further comprises a first aperture 151. The first aperture 151 is a negative space formed through the first sheet 141. The second sheet 142 is a rectangular sheeting. The second sheet 142 is formed from a gas impermeable material. The second sheet 142 further comprises a second aperture 152. The second aperture 152 is a negative space formed through the second sheet 142. The perimeter of the first aperture 151 is congruent to the perimeter of the second aperture 152 such that the first aperture 151 can be overlaid on and aligned with the second aperture 152. The space between the first sheeting 141 and the second sheeting 142 forms the chamber 112. The needle aperture 113 is an aperture formed through the face of the cylinder that forms the shell 111.

The arm 192 inserts into the shell 111 such that the needle aperture 113 is positioned over the vein 193 of the arm 192 that is targeted to receive the hypodermic needle 194. The needle aperture 113 further forms a protected region of the arm 192 that is not placed under pressure as the chamber 112 inflates. The pressure differential formed between the needle aperture 113 and the chamber 112 causes the blood in the arm 192 to move towards the needle aperture 113 causing the vein 193 to enlarge thereby forming an easier target for the insertion of the hypodermic needle 194.

The coating 102 is a neoprene (CAS 9010-98-4) foam applied as a layer to the exterior and interior surfaces of the tubular bladder 101. The coating 102 is formed as an elastomeric structure that protects the arm 192 of the patient 191 from injury. The elastomeric structure of the coating 102 further ensures that pressure applied by the tubular bladder 101 is diffused evenly over the arm 192. The coating 102 acts as an insulator that further keeps the arm 192 warm as the hypodermic needle 194 is inserted.

The connector 103 forms a fluidic connection between the pump mechanism 104 and the tubular bladder 101. Specifically, the connector 103 transports atmospheric gases under pressure into the chamber 112 of the tubular bladder 101 such that the tubular bladder 101 inflates to apply pressure to the arm 192. The connector 103 forms the port component of a plug and port connection that attaches the pump mechanism 104 to the connector 103. The connector 103 comprises a port 121 and a tube 122. The tube 122 is further defined with a first end 171 and a second end 172.

The port 121 is a commercially available port configured for use in transporting gases. The port 121 is sized to receive the plug apparatus 133 of the pump mechanism 104. The port 121 receives pressurized gas from the pump mechanism 104 and transfers the pressurized gas to the tube 122. The tube 122 is a flexible hose that receives pressurized gas from the port 121 and transports the pressurized gas to the chamber 112 of the tubular bladder 101. In the first potential embodiment of the disclosure, the tube 122 is a medical grade hose.

The pump mechanism 104 is a commercially available device that pressurizes atmospheric gases in preparation for transport into the tubular bladder 101. In the first potential embodiment of the disclosure, the pump mechanism 104 is a bulb pump 131 based device often seen on the traditional sphygmomanometer (blood pressure cuff). The pump mechanism 104 comprises a bulb pump 131, a release valve 132, and a plug apparatus 133.

The bulb pump 131 is a commercially available hand pump. The bulb pump 131 comprises a squeezable structure and a one-way valve. Squeezing the structure expels air from the interior of the bulb pump 131. As the bulb pump 131 is released the one-way valve replenishes the expelled air thereby recharging the bulb pump 131 for another squeeze.

The release valve 132 is a valve. The release valve 132 opens the interior of the bulb pump 131 to the atmosphere thereby releasing any pressure built up in both the pump mechanism 104 and the chamber 112 of the tubular bladder 101. The use of the bulb pump 131 and the release valve 132 in this manner is well-known and documented in the medical arts.

The plug apparatus 133 is a structure that is designed to plug into the port 121 of the connector 103. The plug apparatus 133 transports pressurized gas from the pump mechanism 104 to the port 121 of the connector 103. Methods to form the plug apparatus 133 as described in this paragraph are well-known and documented in the medical arts.

The following two paragraphs describe the assembly of the invention 100.

The first sheet 141 lays over the second sheet 142 such that the first aperture 151 aligns with the second aperture 152. The tube 122 lays between the first sheet 141 and the second sheet 142 such that the second end 172 of the tube 122 is within the chamber 112 of the tubular bladder 101. The port 121 attaches to the first end 171 of the tube 122. The plug apparatus 133 attaches the bulb pump 131 to the connector 103.

A first seam 181 forms a gas impermeable seam between the first edge 161 and the fifth edge 165. A third seam 183 forms a gas impermeable seam between the third edge 163 and the seventh edge 167 such that the third seam 183 further seals around the tube 122. A second seam 182 forms a gas impermeable seam between the second edge 162, the sixth edge 166, the fourth edge 164, and the eighth edge 168. A fourth seam 184 forms a gas impermeable seam between the perimeter of the negative space formed by the first aperture 151 and the perimeter of the negative space that is formed by the second aperture 152 to form the needle aperture 113. The first seam 181 is a heat bonded seam. The second seam 182 is a heat bonded seam. The third seam 183 is a heat bonded seam. The fourth seam 184 is a heat bonded seam.

Figure 1:
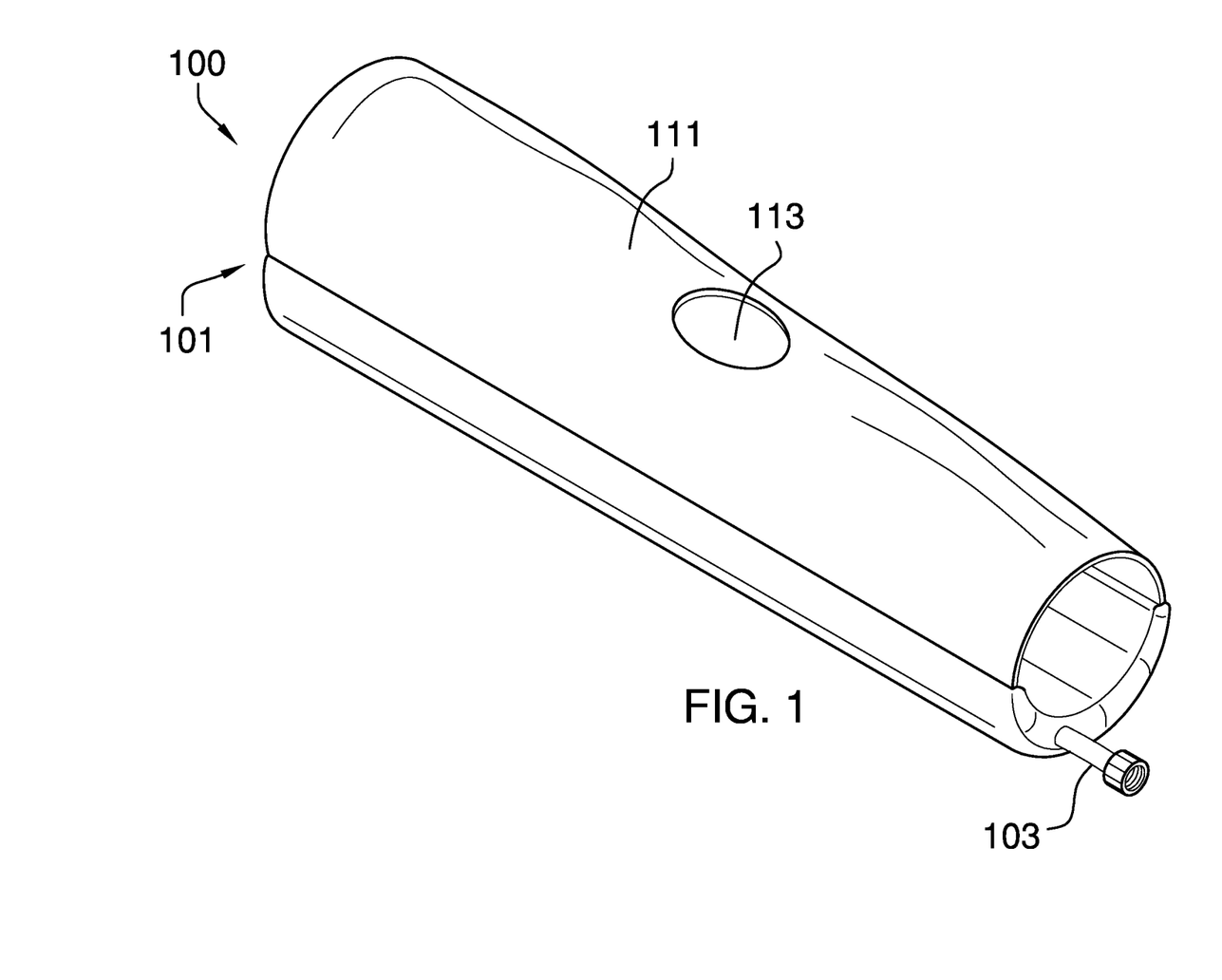
FIG. 1 is a perspective view of an embodiment of the disclosure.
Figure 2:
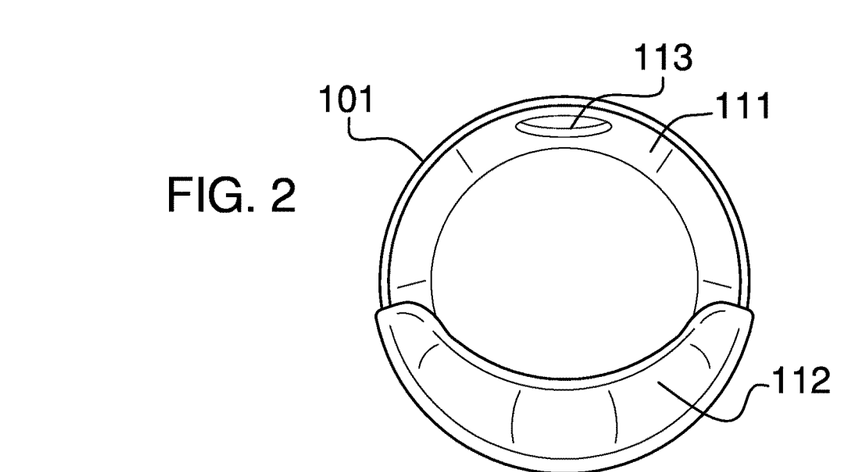
FIG. 2 is a rear view of an embodiment of the disclosure.
Figure 3:
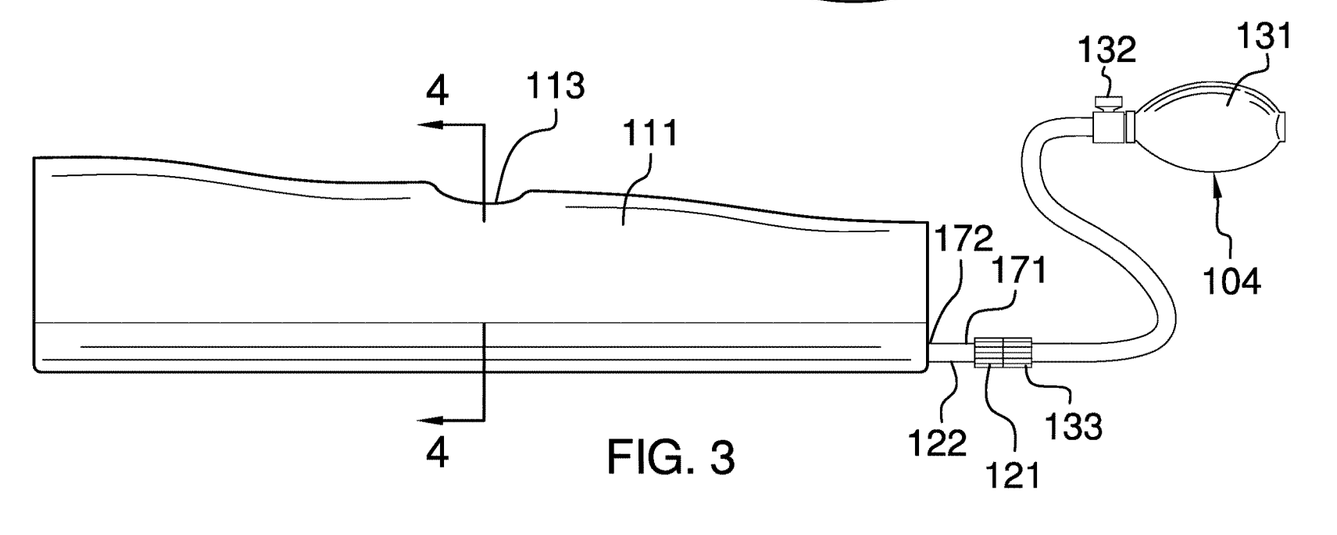
FIG. 3 is a side view of an embodiment of the disclosure.
Figure 4:
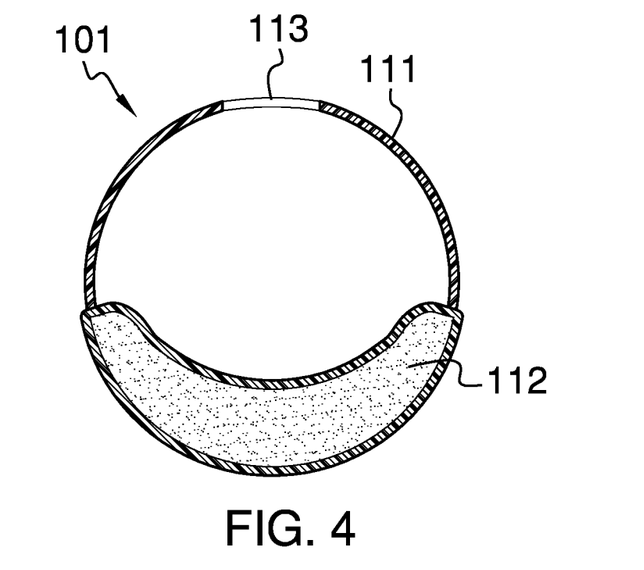
FIG. 4 is a cross-sectional view of an embodiment of the disclosure across 4-4 as shown in FIG. 3.
Figure 5:
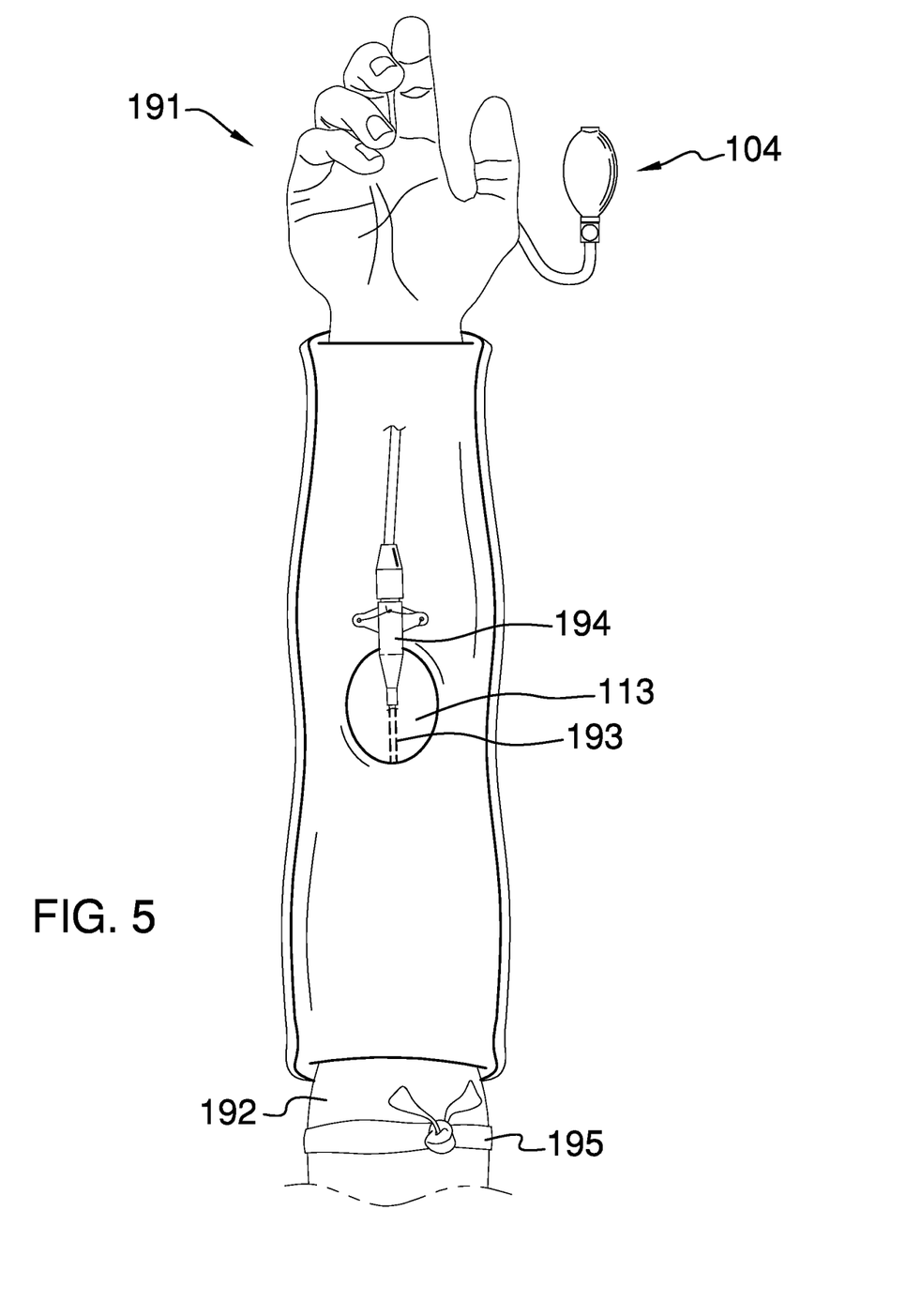
FIG. 5 is an in use view of an embodiment of the disclosure.
Figure 6:
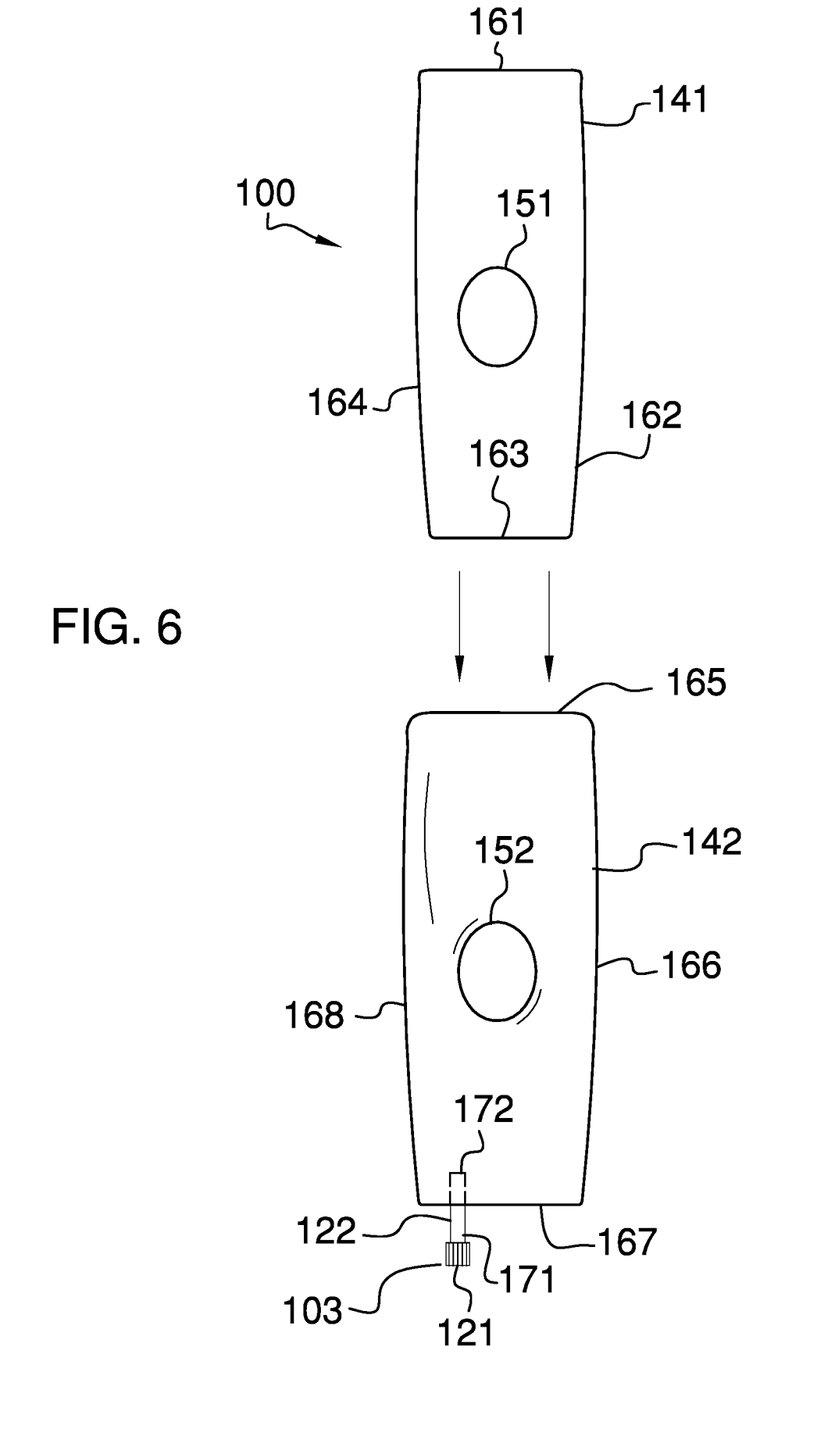
FIG. 6 is a detail view of an embodiment of the disclosure.
Figure 7:
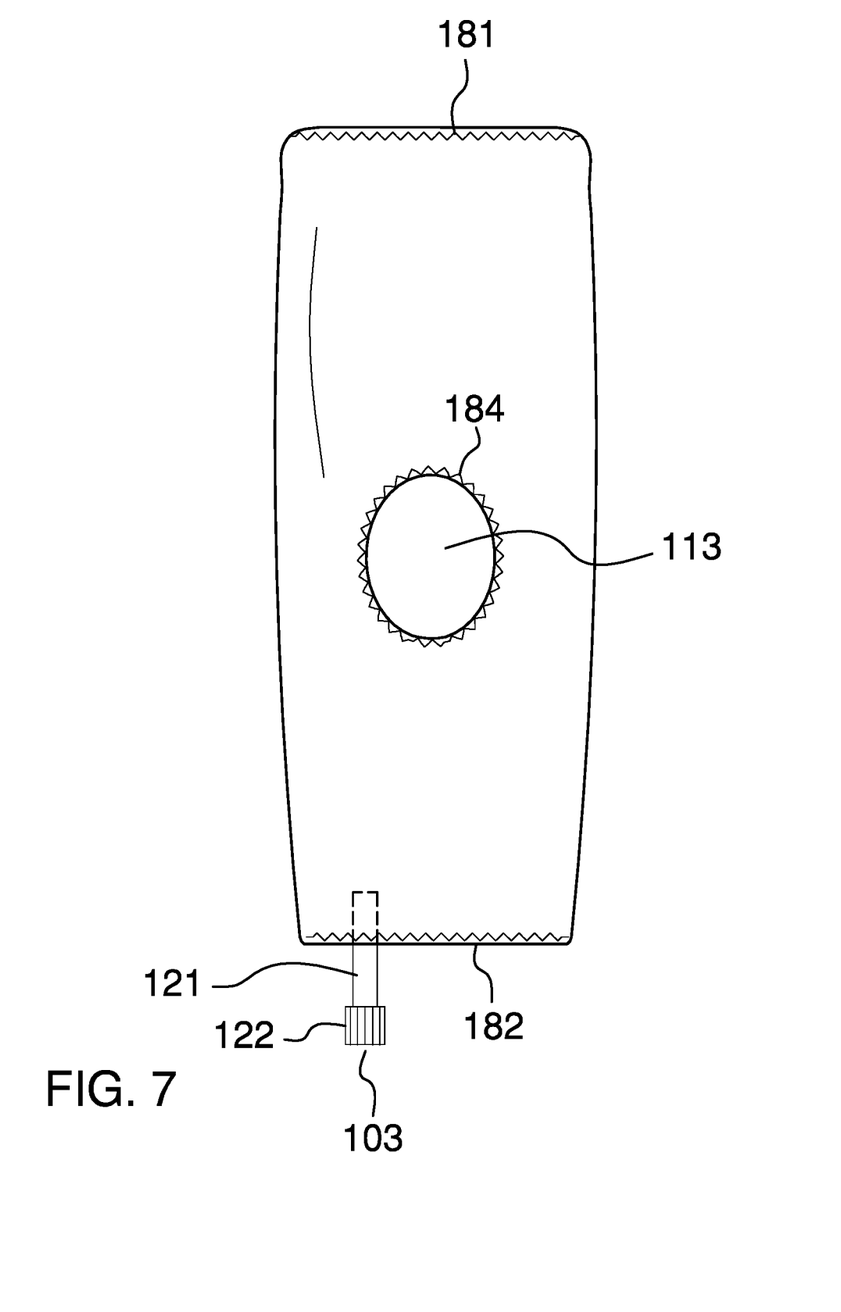
FIG. 7 is a detail view of an embodiment of the disclosure.
Figure 8:
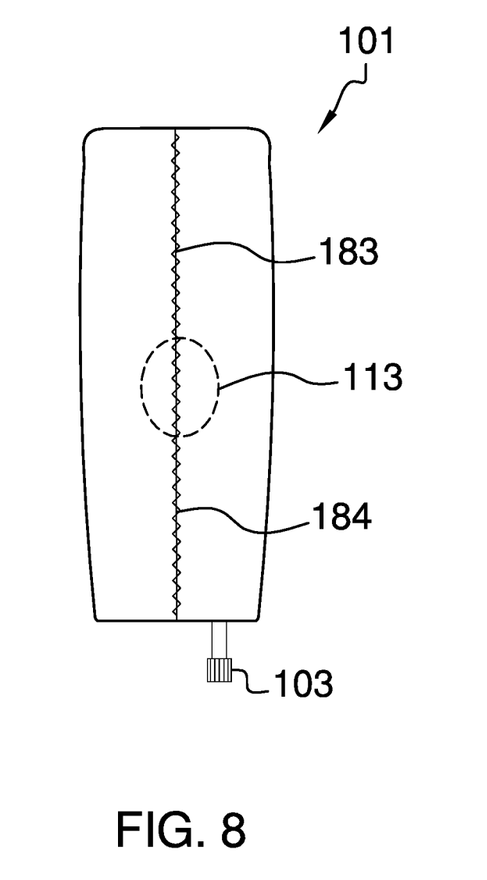
FIG. 8 is a detail view of an embodiment of the disclosure.
Figure 9:
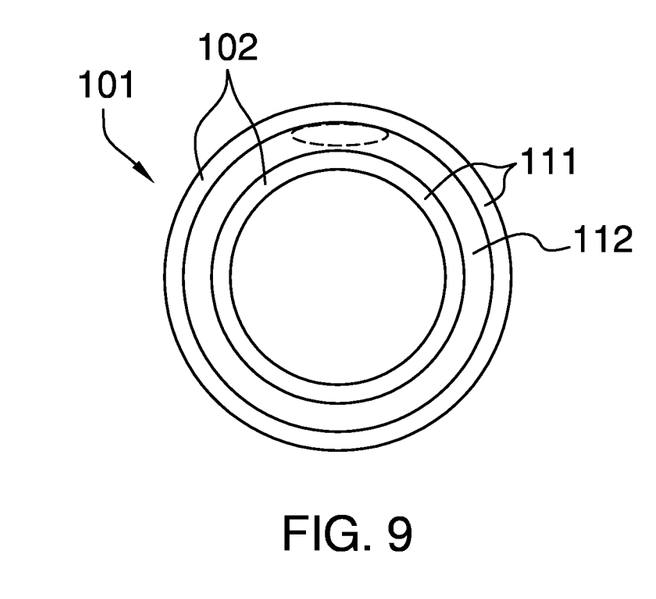
FIG. 9 is a detail view of an embodiment of the disclosure.

This paragraph describes the use of the invention 100. The arm 192 of the patient 191 is tied off with a tourniquet 195. The arm 192 is then inserted into the tubular bladder 101 and the tubular bladder 101 is inflated using the pump mechanism 104. After the tubular bladder 101 is inflated, the hypodermic needle 194 is inserted into the targeted vein 193. The tubular bladder 101 is deflated and removed from the arm 192 of the patient 191. The tourniquet 195 is released.

The following definitions were used in this disclosure:

Align: As used in this disclosure, align refers to an arrangement of objects that are: 1) arranged in a straight plane or line; 2) arranged to give a directional sense of a plurality of parallel planes or lines; or, 3) a first line or curve is congruent to and overlaid on a second line or curve.

Bladder: As used in this disclosure, a bladder is gas impermeable structure. The internal volume of the structure can be varied by: varying the pressure and/or quantity of a gas contained within the bladder; or 2) varying the quantity of a liquid contained within the bladder. Bladders are commonly used for storage of a gas or liquid and as a cushion.

Coating: As used in this disclosure, a coating refers to a substance applied to the exterior surface of an object such that the coating forms a new exterior surface of the object. A coating is commonly said to be formed as a layer. Paint is an example of a common coating material.

Cylinder: As used in this disclosure, a cylinder is a geometric structure defined by two identical flat and parallel ends, also commonly referred to as bases, which are circular in shape and connected with a single curved surface, referred to in this disclosure as the face. The cross section of the cylinder remains the same from one end to another. The axis of the cylinder is formed by the straight line that connects the center of each of the two identical flat and parallel ends of the cylinder. Unless otherwise stated within this disclosure, the term cylinder specifically means a right cylinder which is defined as a cylinder wherein the curved surface perpendicularly intersects with the two identical flat and parallel ends.

Diameter: As used in this disclosure, a diameter of an object is a straight line segment (or a radial line) that passes through the center (or center axis) of an object. The line segment forming the diameter terminates at the perimeter or boundary of the object through which the line segment of the diameter runs.

Elastic: As used in this disclosure, an elastic is a material or object that deforms when a force is applied to it and that is able to return to its relaxed shape after the force is removed. A material that exhibits these qualities is also referred to as an elastomeric material.

Foam: As used in this disclosure, a foam is a mass of gas filled spaces, commonly referred to as bubbles, which can be formed: 1) on or in a liquid or gel; or, 2) in a solid material.

Inner Diameter: As used in this disclosure, the term inner diameter is used in the same way that a plumber would refer to the inner diameter of a pipe.

Negative Space: As used in this disclosure, negative space is a method of defining an object through the use of open or empty space as the definition of the object itself, or, through the use of open or empty space to describe the boundaries of an object.

Neoprene: As used in this disclosure, neoprene is a popular name for polychloroprene (CAS 9010-98-4).

Patient: As used in this disclosure, a patient is a person who is designated to receive a medical treatment, therapy or service. The term patient may be extended to an animal when used within the context of the animal receiving veterinary treatment or services Perimeter: As used in this disclosure, a perimeter is one or more curved or straight lines that bounds an enclosed area on a plane or surface. The perimeter of a circle is commonly referred to as a circumference.

Plug: As used in this disclosure, a plug is an object used: 1) as a barrier to block access to a cavity or an aperture; or, 2) a connection device inserted into a port, cavity, or aperture to attach a first object to a second object.

Port: As used in this disclosure, a port is a cavity formed in an object that is adapted to receive a plug.

Pump: As used in this disclosure, a pump is a mechanical device that uses suction or pressure to raise or move fluids, compress fluids, or force a fluid into an inflatable object. Within this disclosure, a compressor refers to a pump dedicated to compressing a fluid or placing a fluid under pressure.

Seam: As used in this disclosure, a seam is a joining of: 1) a first textile to a second textile; 2) a first sheeting to a second sheeting; or, 3) a first textile to a first sheeting. Potential methods to form seams include, but are not limited to, a sewn seam, a heat bonded seam, an ultrasonically bonded seam, or a seam formed using an adhesive.

Sheeting: As used in this disclosure, sheeting is a material, such as a textile, a plastic, or a metal foil, in the form of a thin flexible layer or layers.

Sleeve: As used in this disclosure, a sleeve is a tube like covering placed over a rod, shaft or other cylindrical object.

Squeeze: As used in this disclosure, to squeeze means to compress an object by hand.

Tradition: As used in this disclosure, a tradition refers to: 1) a set of thoughts or expectations regarding a subject or object; or, 2) a method of using an object; that, 3) is perceived to be widely or commonly shared across a population of people; and that, 4) is perceived to be widely or commonly shared across at least two generations within the population of people.

Tube: As used in this disclosure, a tube is a hollow cylindrical device used for transporting liquids and gases. The line that connects the center of the first base of the cylinder to the center of the second base of the cylinder is referred to as the center axis of the tube or the centerline of the tube. In this disclosure, the terms inner diameter of a tube and outer diameter of a tube are used as they would be used by those skilled in the plumbing arts.

Valve: As used in this disclosure, a valve is a device used to control the flow of a fluid (gas or liquid) through a tube.

With respect to the above description, it is to be realized that the optimum dimensional relationship for the various components of the invention described above and in FIGS. 1 through 9 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

The inventor claims:

1. A medical device comprising:
wherein the medical device comprises a tubular bladder, a connector, and a pump mechanism;
wherein the connector attaches the pump mechanism to the tubular bladder;
wherein the medical device is configured for use with a patient;
wherein the medical device is configured for use with a hypodermic needle; wherein the medical device is adapted to prepare an arm of a patient to receive the hypodermic needle; wherein the tubular bladder is adapted to be placed around the arm in the manner of a sleeve;
wherein the pump mechanism introduces compressed aft into the tubular bladder such that pressure is adapted to be applied to the arm;
wherein the tubular bladder further comprises a needle aperture;
wherein the needle aperture is an aperture formed through the tubular bladder;
wherein the tubular bladder is adapted to be placed such that the needle aperture is adapted to be positioned over a vein of the arm;
wherein the applied pressure to the arm by the tubular bladder is adapted to force blood into an unpressurized region of the vein underneath the needle aperture;
wherein the increase in pressure is adapted to increase the diameter of the vein to make it easier to insert the hypodermic needle into the vein;
wherein the tubular bladder is an inflatable structure that forms a sleeve;
wherein the tubular bladder comprises a shell, a chamber, and the needle aperture;
wherein the chamber is a sealed hollow structure formed within the shell;
wherein the needle aperture is formed through the shell;
wherein the chamber receives pressurized gas from the pump mechanism;
wherein a volume of the chamber increases as the chamber receives the pressurized gas from the pump mechanism;
wherein the shell is a gas impermeable structure;
wherein the shell comprises a first sheet and a second sheet;
wherein the first sheet attaches to the second sheet;
wherein the first sheet is further defined with a first edge, a second edge, a third edge, and a fourth edge;
wherein the second sheet is further defined with a fifth edge; a sixth edge, a seventh edge, and an eighth edge;
wherein the first sheet further comprises a first aperture;
wherein the second sheet further comprises a second aperture;
wherein the first aperture is a negative space formed through the first sheet;
wherein the second aperture is a negative space formed through the second sheet.

2. The medical device according to claim 1 wherein the perimeter of the first aperture is congruent to the perimeter of the second aperture such that the first aperture can be overlaid on and aligned with the second aperture.

3. The medical device according to claim 2
wherein the space between the first sheeting and the second sheeting forms the chamber;
wherein the first aperture and the second aperture forms the needle aperture.

4. The medical device according to claim 3 wherein the connector forms a fluidic connection between the pump mechanism and the tubular bladder.

5. The medical device according to claim 4
wherein the connector comprises a port and a tube;
wherein the port attaches to the tube;
wherein the tube is further defined with a first end and a second end;
wherein the port receives pressurized gas from the pump mechanism and transfers the pressurized gas to the tube;
wherein the tube is a flexible hose that receives pressurized gas from the port and transports the pressurized gas to the chamber of the tubular bladder.

6. The medical device according to claim 5
wherein the pump mechanism comprises a bulb pump, a release valve, and a plug apparatus;
wherein the release valve and plug apparatus attach to the release valve;
wherein the plug apparatus is a structure that plugs into the port of the connector.

7. The medical device according to claim 6
wherein the bulb pump comprises a squeezable structure and a one-way valve;
wherein the release valve is a valve;
wherein the release valve opens the interior of the bulb pump to the atmosphere;
wherein the plug apparatus transports pressurized gas from the pump mechanism to the port of the connector.

8. The medical device according to claim 7
wherein the first sheet lays over the second sheet such that the first aperture aligns with the second aperture;
wherein the tube lays between the first sheet and the second sheet such that the second end of the tube is within the chamber of the tubular bladder;
wherein the port attaches to the first end of the tube;
wherein the plug apparatus attaches the bulb pump to the connector;
wherein a first seam forms a gas impermeable seam between the first edge and the fifth edge;
wherein a third seam forms a gas impermeable seam between the third edge and the seventh edge such that the third seam further seals around the tube;
wherein a second seam forms a gas impermeable seam between the second edge, the sixth edge, the fourth edge, and the eighth edge;

wherein a fourth seam forms a gas impermeable seam between the perimeter of the negative space formed by the first aperture and the perimeter of the negative space that is formed by the second aperture to form the needle aperture.

9. The medical device according to claim 8
wherein the first seam is a heat bonded seam;
wherein the second seam is a heat bonded seam;
wherein the third seam is a heat bonded seam;
wherein the fourth seam is a heat bonded seam.

10. The medical device according to claim 7
wherein the medical device further comprises a coating;
wherein the coating is an elastomeric material;
wherein the coating forms a cushion;
wherein the coating is adapted to evenly distribute the pressure from the tubular bladder over the surface area of the arm,
wherein the coating creates an insulated layer around the arm.

11. The medical device according to claim 10
wherein the first sheet lays over the second sheet such that the first aperture aligns with the second aperture;
wherein the tube lays between the first sheet and the second sheet such that the second end of the tube is within the chamber of the tubular bladder;
wherein the port attaches to the first end of the tube;
wherein the plug apparatus attaches the bulb pump to the connector;
wherein a first seam forms a gas impermeable seam between the first edge and the fifth edge;
wherein a third seam forms a gas impermeable seam between the third edge and the seventh edge such that the third seam further seals around the tube;
wherein a second seam forms a gas impermeable seam between the second edge, the sixth edge, the fourth edge, and the eighth edge;
wherein a fourth seam forms a gas impermeable seam between the perimeter of the negative space formed by the first aperture and the perimeter of the negative space that is formed by the second aperture to form the needle aperture.

12. The medical device according to claim 11
wherein the first seam is a heat bonded seam;
wherein the second seam is a heat bonded seam;
wherein the third seam is a heat bonded seam;
wherein the fourth seam is a heat bonded seam;
wherein the coating is a neoprene foam.

\* \* \* \* \*